United States Patent [19]

Zimmerman

[11] Patent Number: 4,806,566

[45] Date of Patent: Feb. 21, 1989

[54] ANTI-GRAM POSITIVE BACTERIA TRI-YNE CARBONATES

[75] Inventor: Sheldon B. Zimmerman, Springfield, N.J.

[73] Assignee: Merck & Co., Inc., Rahway, N.J.

[21] Appl. No.: 53,921

[22] Filed: May 26, 1987

[51] Int. Cl.$^4$ ............................................. A61K 31/335
[52] U.S. Cl. ...................................................... 514/467
[58] Field of Search ............................................ 514/467

[56] References Cited

U.S. PATENT DOCUMENTS

| | | | |
|---|---|---|---|
| 4,331,604 | 5/1982 | Renga et al. | 549/229 |
| 4,332,729 | 6/1982 | Renga et al. | 549/229 |

*Primary Examiner*—Glennon H. Hollrah
*Assistant Examiner*—S. Treanor
*Attorney, Agent, or Firm*—Richard S. Parr; Hesna J. Pfeiffer

[57] ABSTRACT

The invention relates to the tri-yne carbonate of formula I which has activity against gram positive bacteria. Such compound can be produced by isolating it from the fermentation broth of ATCC-53614, ATCC-53615 or ATCC-53616.

4 Claims, 1 Drawing Sheet

ANTI-GRAM POSITIVE BACTERIA TRI-YNE CARBONATES

BACKGROUND OF THE INVENTION

The invention relates to the tri-yne carbonate of formula I which has activity against gram positive bacteria. Such compound can be produced by isolating it from the fermentation broth of ATCC-53614, ATCC-53615 or ATCC-53616.

SUMMARY OF THE INVENTION

This invention relates to the compound 5-(1-hydroxy-2,4,6-heptatriynyl)-2-oxo-1,3 dioxolane and its pharmaceutically acceptable salts, which has the general structure of formula I:

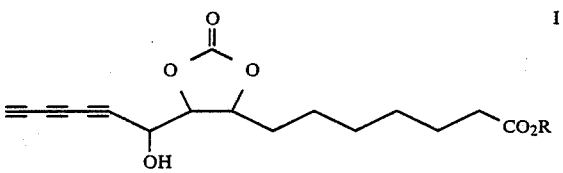

wherein R is H or a pharmaceutically acceptable salt. The compounds of formula I are useful as gram positive antibacterial agents.

DETAILED DESCRIPTION OF THE INVENTION

Figure 1:
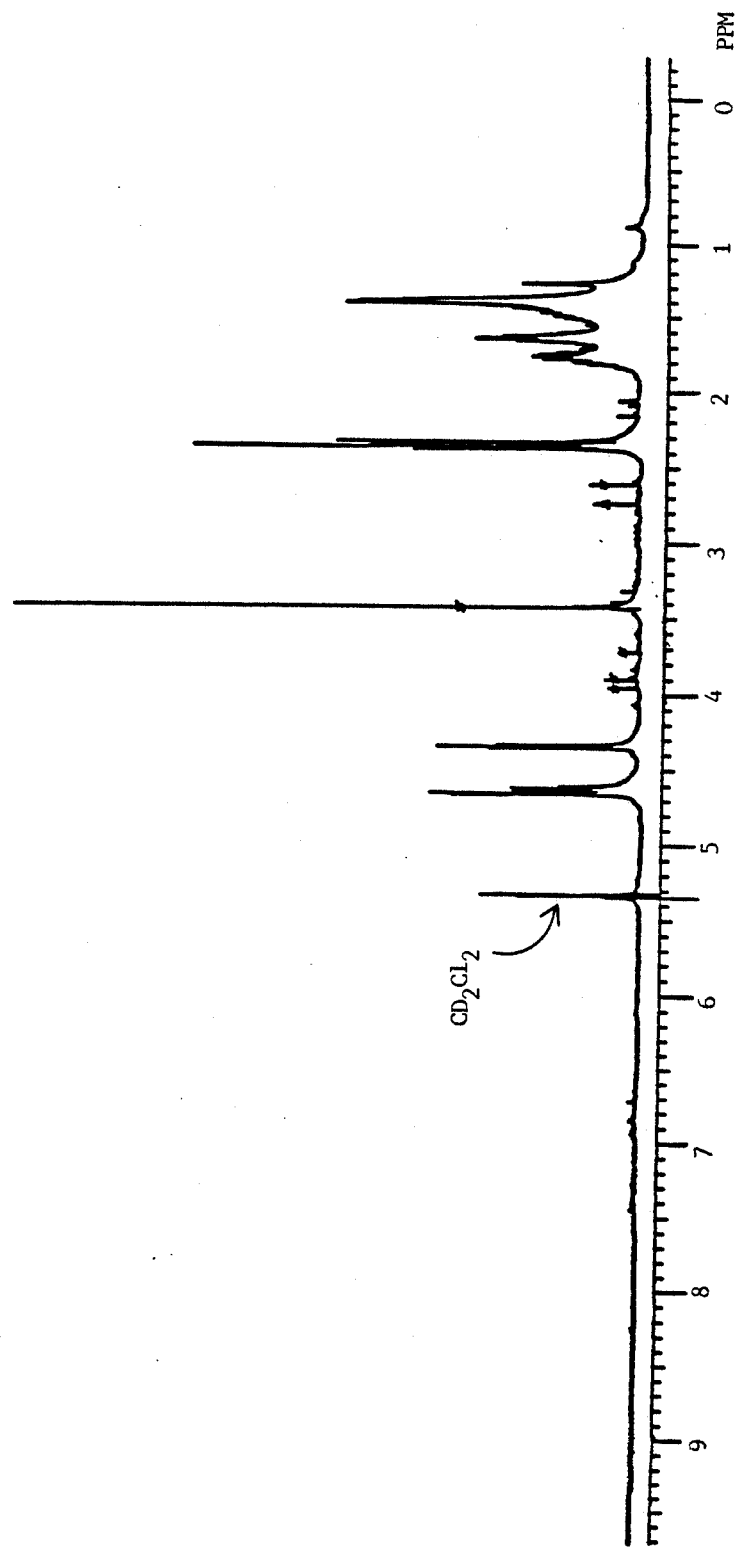

The tri-yne carbonate of Formula I has activity against gram positive bacteria. For example, the compounds of this invention are useful against the gram positive bacteria Staphlococcus and Streptococcus. Specifically, the compounds of formula I are effective against *Staphylococcus aureus,* methicillin-resistant *Staphylococcus aureus* and *Streptococcus faecalis.*

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

Effective dosage levels for the compounds of formula I would be on the order of 5 mg/kg to 20 mg/kg in mammals. The compounds of formula I can be administered intravenously, intramuscularly, or subcutaneously, either alone or in combination with a pharmaceutical carrier. The ultimate choice of route and dose should be made by an attending physician and based upon the patient's unique condition.

Combinations of the compounds of formula I with appropriate pharmaceutical carriers are accomplished by methods well known to the pharmacist's art. For purposes of subcutaneous (s.c.) administration, solutions of the compounds of formula I are generally employed, for example with sterile aqueous or alcoholic solutions. Such solutions should be suitably buffered if necessary and the liquid diluent may first be rendered isotonic with saline or glucose. These aqueous and alcoholic solutions are also suitable for intravenous (i.v.) injections.

The compound of formula I can be prepared by growing under controlled conditions the microorganism ATCC-53614, ATCC-53615 or ATCC-53616, with ATCC-53614 being preferred because it produces the largest quantities of the compound of formula I. The compound is obtained by fermentation of one of said microorganisms followed by isolation of the compound, all as described hereinbelow.

Based upon taxonomic studies, ATCC-53614 and ATCC-53615 are new strains of the species *Streptoverticillium hiroshimense.* ATCC-53616 is a strain of the genus Nocardia. A sample of ATCC-53614, ATCC-53615 and ATCC-53616 has been deposited, without restriction as to availability, in the permanent culture collection of the American Type Culture Collection at 12301 Parklawn Dr., Rockville, Md. 20852 and have been assigned the accession numbers that such microorganisms have been referred to herein.

The morphological and cultural characteristics of ATCC-53614, ATCC-53615 and ATCC-53616 are as follows:
(V=vegetative growth, A=aerial mycelium, SP=soluble pigment)

ATCC-53615

Morphology: Sporophores form short branches produced in a verticil or whorl at intervals along the aerial mycelium. These branches in turn produce several secondary branches that form straight chains of 10–15 spores. Spores are cylindrical, 0.9×1.2–1.7 microns. Spore surface is smooth.

Yeast extract-malt extract agar (ISP Medium 2)

V: Reverse—dark brown with vectors of dark red
A: Deep pink mixed with red and rose-beige vectors
SP: None Oatmeal agar (ISP Medium 3)

V: Reverse—dark brown with vectors of dark red
A: Velvety, dark pink with pinkish-white & rose-beige vectors and red flecks
SP: None Inorganic salts-starch agar (ISP Medium 4)

V: Reverse—dark reddish brown with vectors of deep pink
A: Deep pink mixed with rose-beige and white
SP: None Glycerol asparagine agar (ISP Medium 5)

V: Reverse—dark reddish brown
A: Rose-beige with vectors of deep rose
SP: None

Peptone-iron-yeast extaact agar (ISP Medium 6)

V: Brown
A: None
SP: Medium brown
Melanin: Dark brown pigment produced in tryptone-yeast extract broth, light brown pigment produced in tyrosine agar and peptone-iron-yeast extract agars Tyrosine Agar (ISP Medium 7)

V: Reverse—brown edged with reddish-brown
A: rose-beige mixed with pink and white
SP: Medium brown

Czapek-Dox Agar

V: Colorless, flat
A: Sparse, white
SP: None

Carbon utilization
  Pridham-Gottlieb basal medium (ISP Medium 9) +
  1% carbon source;
  + = growth; ± = growth poor or questionable;
  − = no growth as compared to negative control
  (no carbon source)

| | |
|---|---|
| Glucose | + |
| Arabinose | − |
| Cellulose | − |
| Fructose | ± |
| Inositol | + |
| Lactose | ± |
| Maltose | + |
| Mannitol | − |
| Mannose | + |
| Raffinose | ± |
| Rhamnose | − |
| Sucrose | ± |
| Xylose | ± |

Temperature range (Yeast extract-dextrose + salts agar)

| | |
|---|---|
| 28° C. | Good growth and sporulation |
| 37° C. | good vegetative growth; moderate aerial growth |
| 42° C. | Moderate vegetative growth; no aerial |
| 50° C. | No growth |

Oxygen requirements (Stab culture in yeast extract-dextrose + salts agar)
  Aerobic All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

ATCC 53614

Morphology: Sporophores form short branches produced in a verticil or whorl at intervals along the aerial mycelium. These branches in turn produce several secondary branches that form straight chains of 10–15 spores. Spores are cylindrical, 0.9×1.2–1.7 microns (970x). Spore surface is smooth (TEM).

Yeast extract-malt extract agar (ISP Medium 2)

V: Reverse—dark red
A: Rose-beige
SP: None

Oatmeal agar (ISP Medium 3)

V: Reverse—deep red
A: Rose-beige
SP: None

Inorganic salts-starch agar (ISP Medium 4)

V: Reverse—deep red
A: Rose-beige
SP: None

Glycerol asparagine agar (ISP Medium 5)

V: Reverse—dark brown with flecks and vectors of deep red
A: Pinkish-beige mixed with white and vector of deep pink
SP: None

Peptone-iron-yeast extract agar (ISP Medium 6)

V: Tan with red flecks
A: None
SP: Lt. brown
Melanin: Positive on peptone-iron-yeast extract agar and tryptone - yeast extract broth

Tyrosine Agar (ISP Medium 7)

V: Reverse—dark red with vectors of lighter red
A: Pinkish-white with vectors of light pink
SP: very light brown

Czapek-Dox Agar

V: moderate, white
A: moderate, white
SP: None

Carbon utilization
  Pridham-Gottlieb basal medium (ISP Medium 9) +
  1% carbon source;
  + = growth; ± = growth poor or questionable;
  − = no growth as compared to negative control
  (no carbon source)

| | |
|---|---|
| Glucose | + |
| Arabinose | ± |
| Cellulose | − |
| Fructose | + |
| Inositol | + |
| Lactose | ± |
| Maltose | + |
| Mannitol | + |
| Mannose | + |
| Raffinose | ± |
| Rhamnose | − |
| Sucrose | ± |
| Xylose | ± |

Temperature range (Yeast extract-dextrose + salts agar)

| | |
|---|---|
| 28° C. | Good growth and sporulation |
| 37° C. | Moderate growth and sporulation |
| 42° C. | No growth |
| 50° C. | No growth |

Oxygen requirements (Stab culture in yeast extract-dextrose + salts agar)
  Aerobic All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

ATCC-53616

Morphology: Vegatative hyphae were fully developed with branching. Fragmentation of hyphae occured in older cultures.

Yeast extract-malt extract agar (ISP Medium 2)

V: Reverse—dull golden yellow
A: Moderate, whitish
SP: None

Oatmeal agar (ISP Medium 3)

V: Tan
A: sparse, grayish white
SP: None

Inorganic salts-starch agar (ISP Medium 4)

V: Reverse—dull golden-yellow
A: Moderate, white to creamish-white

SP: None

Glycerol asparagine agar (ISP Medium 5)

V: Tan
A: Sparse, whitish
SP: None

Peptone-iron-yeast extract agar (ISP Medium 6)

V: Tan
A: None
SP: None
Melanin: Negative

Tyrosine Agar (ISP Medium 7)

V: Tan
A: None
SP: None

Czapek-Dox Agar

V: Very thin, colorless growth
A: None
SP: None

---

Carbon utilization

Pridham-Gottlieb basal medium (ISP Medium 9) + 1% carbon source; + = growth; ± = growth poor or questionable; − = no growth as compared to negative control (no carbon source)

| | |
|---|---|
| Glucose | + |
| Arabinose | − |
| Cellulose | − |
| Fructose | + |
| Inositol | + |
| Lactose | − |
| Maltose | + |
| Mannitol | − |
| Mannose | + |
| Raffinose | − |
| Rhamnose | − |
| Sucrose | − |
| Xylose | − |

Temperature range (Yeast extract-dextrose + salts agar)

| | |
|---|---|
| 28° C. | Good vegetative and aerial growth |
| 37° C. | Good vegetative; sparse aerial |
| 42° C. | No growth |
| 50° C. | No growth |

Oxygen requirements (Stab culture in yeast extract-dextrose + salts agar)

Aerobic

---

All readings taken after three weeks at 28° C. unless noted otherwise. pH of all media approximately neutral (6.8–7.2).

It is to be understood that for the production of the compound of formula I, the present invention is not limited to the use of ATCC-53614, ATCC-53615 or ATCC-53616. It is especially desired and intended to include the use of natural or artificial mutants produced from the described organisms, or other variants of ATCC-53614, ATCC-53615 or ATCC-53616 as far as they can produce the compound of formula I. The artificial production of mutants may be achieved by a conventional operation such as X-ray or ultraviolet (UV) radiation, or by the use of chemical mutagens such as; nitrogen mustards, nitrosoguanidine, camphor and the like, or by means of recombinant DNA technology.

The compound of formula I can be produced by utilizing a preserved source of ATCC-53614, ATCC-53615 or ATCC-53616 under controlled aerobic conditions in a liquid nutrient medium as follows. The preserved source is utilized to inoculate a liquid nutrient medium containing sources of carbon, nitrogen, phosphorus, calcium and magnesium and other elements necessary for life. This medium is incubated at 28° C. The flask containing the culture and liquid nutrient medium is incubated with agitation on a rotary shaker at 220 RPM. After 48 hours, when growth is abundant, the culture growth is used to inoculate a flask containing a medium which supports production of the product.

These production media are inoculated with the culture growth and are incubated at 28° C. for 4 days with agitation at 180 to 220 RPM, most often 220 RPM.

Such media contain carbon sources such as glycerol, dextrose, cottonseed oil, cod liver oil or corn gluten. They contain nitrogen and sulfur sources such as beef extract, yeast extract, ardamine pH, Edamine, Hycase and corn gluten. Also included are inorganic ions such as calcium, as well as some inert materials as celite.

In order to isolate the compound of formula I, the fermentation broth must be clarified by filtration. The compounds of interest reside in the broth filtrate. The crude product may be purified by chromatography using an appropriate adsorbent such as polymeric organic based resins such as Amberlite XAD-2 or Mitsubishi HP-20, silica gel and hydroxypropyl cross linked dextran gels such as Pharmacia LH-20. The compound of formula I is eluted from the adsorbents with suitable solvents or mixture of solvents. Solvent extraction is also used.

The following examples illustrate the preparation of the compound of the invention and should not be construed as limiting the invention.

The composition of media employed in the following examples are listed below. Media are prepared in a 250 ml Erlenmeyer flask. The contents are sterilized with steam at 121° C., 15 pounds pressure for 20 minutes.

| BAM II & Celite | |
|---|---|
| Yeast Extract | 1 g. |
| Beef Extract | 1 g. |
| Hycase | 2 g. |
| Glucose | 10 g. |
| MOPS | 11.6 g. |
| Celite | 5 g. |
| Distilled $H_2O$ | 1,000 ml. |
| pH | 7.0–7.2 using NaOH |
| NPA-2 | |
| Corn Gluten | 5 g. |
| Edamine | 2.5 g. |
| Yeast Extract | 5 g. |
| Glucose | 10 g. |
| $CaCO_3$ | 5 g. |
| Distilled $H_2O$ | 1,000 ml. |
| pH | 7.2–7.4 using NaOH |
| KH | |
| Tomato Paste | 20 g. |
| Primary Yeast | 10 g. |
| Dextrin | 20 g. |
| $CoCl_2.6H_2O$ | 5 g. |
| Distilled $H_2O$ | 1,000 ml. |
| pH | 7.2–7.4 using NaOH |
| KE | |
| Dextrose | 1 g. |
| Starch | 10 g. |
| Beef Extract | 3 g. |
| Ardamine pH | 5 g. |
| NZ Amine Type E | 5 g. |
| $MgSO_4.7H_2O$ | 0.05 g. |
| Phosphate Buffer | 2.0 ml. |
| $CaCO_3$ | 0.5 g. |
| Distilled $H_2O$ | 1,000 ml. |
| pH | 7.0–7.2 using NaOH |
| Phosphate Buffer | |
| $KH_2PO_4$ | 91 g. |
| $Na_2HPO_4$ | 95 g. |

-continued

| | |
|---|---|
| Distilled H$_2$O | 1,000 ml. |
| pH = 7 | |
| LP | |
| Beef Extract | 6 g. |
| Glycerol | 8.0 ml. |
| Cottonseed Oil | 1.0 ml. |
| Cod Liver Oil | 1.0 ml. |
| Ardamine pH | 0.4 g. |
| Distilled H$_2$O | 1,000 ml |
| pH = 7.0 | |

EXAMPLE 1

Preparation of the Compound of Formula I (I) (a) Fermentation of ATCC-53614

A culture of ATCC-53614 is inoculated from an L-tube (lyophilized tube) into a 250 ml baffled erlenmeyer flask containing 44 ml. of KE seed medium and grown for two days at 28° C. and shaken in a rotary shaker (2 inch throw) at 220 rpm. Two ml of the grown seed medium is then inoculated into a 250 ml unbaffled erlenmeyer flask containing about 54 ml. of the production medium LP and grown at 28° C. and shaken in a rotary shaker (2 inch throw) for four days at 220 rpm. The compound of formula I is contained in this broth.

(b) Fermentation of ATCC-53615

A culture of ATCC-53615 is inoculated from an L-tube into a 250 ml erlenmeyer flask containing 54 ml of BAMII and celite seed medium. The flask is incubated at 28° C. and shaken in a rotary shaker (2 inch throw) at 220 rpm for 48 hours. Then 10 ml from this flask is used to inoculate a two liter baffled erlenmeyer flask containing 250 ml of NPA-2 production medium. This flask is incubated at 28° C., and shaken in a rotary shaker (2 inch throw) for 96 hours at 180 rpm. The compound of formula I is contained in this broth.

(c) Fermentation of ATCC-53616

A culture of ATCC-53616 is inoculated from an L-tube into a 250 ml baffled erlenmeyer flask containing 54 ml of KE medium. The flask was then placed on a rotary shaker (2 inch throw) and shaken at 220 rpm for 2 days in a 28° C. room. Two ml of the broth were then used to inoculate a 250 ml unbaffled erlenmeyer flask containing 44 ml of KH medium. This flask was then placed on a rotary shaker (2 inch throw) at 28° C. and shaken for four days at 220 rpm.

(II) Isolation of the Compound of Formula I

The compound of formula I can be isolated from each of the broths of ATCC-53614, ATCC-53615 and ATCC-53616 by the following procedure. It should be noted that the following isolation procedure can be utilized for varying volumes of whole broth by adjusting proportionately the volumes of the solvents and adsorbents.

Isolation of the free acid of formula I (a) Approximately 2180L of whole broth from a fermentation batch was harvested at 48 hours. The broth was clarified by filtration using Supercel as a filter aid, followed by a water wash. The 2200L filtered broth at pH7 was adsorbed on 120L of Mitsubishi Diaion HP-20 resin at 4L/minute. The resin was washed with 120L of distilled deionized water at the same rate. Antibiotic activity was eluted from the resin with 15×10L fractions of 60:40 acetone-water. The rich eluate fractions (5-12) were combined (80L) and extracted with 2×80L ethyl acetate. Extract 1 (130L) and extract 2 (100L) were combined and dried over anhydrous sodium sulfate. The drying agent was removed by filtration and the filtrate was concentrated under vacuum to 3.75L. The concentrated extract contained 6.5 g of the free acid of formula I at about 5% pure.

(b) 800 ml of ethylacetate extract (approximately 1.39 g of the free acid of formula I) from Step a was evaporated to an oily residue and immediately taken up in methylene chloride to a volume of 100 ml. The methylene chloride solution was applied to a 200 g column of E. Merck silica gel grade 62 (60-200 mesh), equilibrated in methylene chloride. The column was washed with 2×500 ml of methylene chloride and then eluted with 5:95 methanol-methylene chloride, taking 250 ml fractions. The free acid of formula I was eluted with the 5:95 methanol-methylene chloride. Fractions 3 and 4 contained 1.0 g (~70% yield) of the free acid of formula I at ~10% pure.

(c) The silica gel rich eluates 3 and 4 from Step b were evaporated to about 12 ml (methanol). 120 ml of methylene chloride and 120 ml of hexane was added to provide the feed for a 900 ml Pharmacia Sephadex LH-20 column equilibrated in 10:10:1 hexanemethylene chloride-methanol. After a 360 ml void volume fraction, four 900 ml (1 column volume) fractions and 30×250 ml fractions were collected. Based on HPLC and bioassay, fraction 13-25 (250 ml each) contained 0.9 g of substantially pure free acid of formula I.

(d) Due to the instability of the free acid of the compound of formula I to concentration, an alternate method was used to provide concentrated solutions. LH20 fractions 13-25 from Step C, 3250 ml, was extracted with 500 ml of 0.1M potassium phosphate buffer pH 7.2. The compound was extracted into the aqueous layer, 620 ml, which was reextracted with 200 ml of methylene chloride at pH 4.5. The methylene chloride extract was dried over anhydrous sodium sulfate. The extraction volumes could be adjusted to provide varying concentrations of the free acid of the compound of formula I in methylene chloride.

(e) Preparation of Sodium Salt of the Compound of Formula I

In order to provide aqueous solutions of the sodium salt of the compound of formula I, the following method was used. 110 ml of LH-20 rich cut (10:10::1) was extracted with 50 ml of water, the pH carefully adjusted to 7.5 with dilute sodium hydroxide. The aqueous layer was evaporated under reduced pressure to remove residual organic solvent, yielding an aqueous solution of the sodium salt of the compound of formula I.

III Analytical Data

All three isolates were shown by HPLC and HRMS to be identical.

Analytical data for the compound of formula I isolated from ATCC-53616 is as follows:

1. Mass Spectral Data

Mass spectral data were obtained on MAT 212 mass spectrometer at 90 ev in the electron impact mode. High resolution data were obtained on the same instrument using the peak matching method.

HRMS gave a molecular formula $C_{17}H_{18}O_6.T_2$ (calc. 462.1894; found 462.1882) upon trimethylsilylation with pyridine: BSTFA (1:1) at 100° C. for 1 hour. Abundant mass ions were found at m/z 175.0574 corresponding to $C_7H_3O.T_1$ (calc. 175.0579). [T=$C_3H_8Si$=72.0395].

2. $^1$H NMR Spectrum

The spectrum is in FIG. I. The spectrum has been recorded in $CD_2Cl_2$ at ambient room temperature on a Varian XL400 spectrometer. Chemical shifts are shown in ppm relative to tetramethylsilane (TMS) at zero ppm using the solvent peak at δ5.32 as internal reference.

3. $^{13}$C NMR Data

The spectrum was recorded in $CD_2Cl_2$ at ambient room temperature at 75 MHz on a Varian XL400 spectrometer. Chemical shifts are given in ppm relative to tetramethylsilane at zero ppm using the solvent peak at 53.8 ppm as internal reference.

In agreement with HRMS data, 17 carbons are observed with the following chemical shifts: 24.4, 24.8, 28.90, 28.95, 33.8, 34.8, 59.0, 63.2, 64.3, 67.7, 69.0, 71.9, 72.9, 78.7, 81.7, 154.1, 178.0 ppm Infrared Data A difference infrared spectrum was measured in dichloromethane on a Nicolet FT-1R instrument, model 7199. Strong bands were observed at 1806 (carbonate) and 1742 (COOH) cm$^{-1}$.

EXAMPLE II

The free acid of the compound of formula I was prepared as aqueous solutions at a concentration of 1.28 mg/ml. Comparative agents vancomycin and streptomycin were prepared at 1.28 mg/ml in Sorensens' buffer, pH 7.

Each of the drugs was serially diluted twofold in 20×100 mm sterile petri dishes with the aid of a Pipetman. To each plate containing 1 ml of the antibiotic dilution was added 9 ml molten trypticase soy agar (TSA) (BBL) to yield final drug concentrations ranging from 128-0.031 mcg/ml. Plates were swirled to mix, allowed to solidify at room temperature and were stored overnight at 5° C.

Cultures were grown in trypticase soy broth (TSB) for 16 hours at 35° C. They were diluted 1-100 in TSB to obtain an inoculum of $10^4$ cfu/spot when plated using a Denley multipoint inoculator calibrated to deliver 0.0015 ml. Inoculated plates were incubated for 24 hours at 35° C.

The minimum inhibitory concentration (MIC) was defined as the lowest concentration that allowed no growth or a barely visible haze.

The results were as follows:

| Microorganism | MIC. mcg/ml Free Acid of the Compound of Formula I | Streptomycin | Vancomycin |
|---|---|---|---|
| Streptococcus faecalis | 0.500 | | 4.000 |
| S. faecalis | 0.500 | | 2.000 |
| S. faecalis | 0.500 | | 4.000 |
| Staphyloccocus aureus methicillin-resistant | 0.500 | | 2.000 |
| S. aureus Meth-R | 0.500 | | 2.000 |
| S. aureus Meth-R | 0.500 | | 2.000 |
| S. aureus Meth-R | 0.500 | | 2.000 |
| S. aureus Meth-R | 0.500 | | 1.000 |
| S. aureus Meth-R | 0.500 | | 2.000 |
| S. aureus Meth-R | 0.500 | | 2.000 |
| S. aureus Meth-R | 0.500 | | 2.000 |
| S. aureus Meth-R | 0.500 | | 2.000 |
| S. aureus Meth-R | 0.500 | | 2.000 |
| S. arueus | 1 | 116 | |
| S. arueus | 1 | 116 | |
| S. faecalis | 4 | >128 | |

What is claimed is:

1. A method of treating gram positive bacterial infections in mammals which comprises administering there to a therapeutically effective amount of a compound represented by the structural formula:

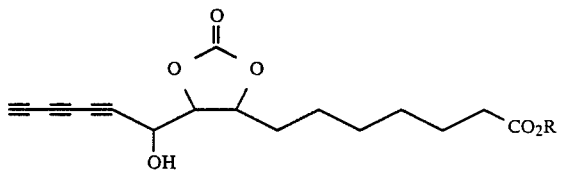

wherein R is hydrogen or a pharmaceutically acceptable salt thereof.

2. The method of claim 1 wherein said gram positive bacterial infection is selected from the group consisting of Staphylococcus and Streptococcus.

3. The method of claim 2 wherein said Staphlococcus is selected from the group *Staphylococcus aureus*, methicillin - resistant *Staphylococcus aureus* and said Streptococcus is *Streptococcus faecalis*.

4. The method of claim 1 wherein said compound is administered with a pharmaceutical carrier.

* * * * *